US010299996B2

(12) United States Patent
Weissbrodt et al.

(10) Patent No.: US 10,299,996 B2
(45) Date of Patent: May 28, 2019

(54) ACTIVE INGREDIENT CAPSULES (71) Applicant: Symrise AG, Holzminden (DE)

(72) Inventors: Jenny Weissbrodt, Holzminden (DE); Frank Aickele, Holzminden (DE); Ralf Bertram, Holzminden (DE)

(73) Assignee: Symrise AG, Holzminden (DE)

(*) Notice: Subject to any disclaimer, the term of this patent is extended or adjusted under 35 U.S.C. 154(b) by 6 days.

(21) Appl. No.: 15/030,521

(22) PCT Filed: Oct. 18, 2014

(86) PCT No.: PCT/EP2014/072382
§ 371 (c)(1),
(2) Date: Apr. 19, 2016

(87) PCT Pub. No.: WO2015/059062
PCT Pub. Date: Apr. 30, 2015

(65) Prior Publication Data
US 2016/0262992 A1 Sep. 15, 2016

(30) Foreign Application Priority Data

Oct. 22, 2013 (EP) ..................................... 13189795

(51) Int. Cl.
A61K 8/11 (2006.01)
A61K 8/73 (2006.01)
(Continued)

(52) U.S. Cl.
CPC ................ A61K 8/11 (2013.01); A23L 33/10 (2016.08); A23L 33/17 (2016.08); A23P 10/30 (2016.08);
(Continued)

(58) Field of Classification Search
CPC .................................................. A23V 2002/00
See application file for complete search history.

(56) References Cited

U.S. PATENT DOCUMENTS 4,376,113 A   8/1983  Suglia et al.
4,402,856 A * 9/1983  Schnoring ............... A61K 8/11
                                                        252/299.01
(Continued)

FOREIGN PATENT DOCUMENTS

EP        038985 A1    10/1984
EP        0126583 A1 * 11/1984  ............. A01N 25/28
(Continued)

OTHER PUBLICATIONS

Zhang et al. "Tannic acid cross-lined gelation-gum arabic coacervate microspheres for sustained release of allyl isothiocyanate. Characterization and in vitro release study," Food Research International vol. 44, No. 4, Feb. 27, 2011, pp. 1000-1007.
(Continued)

Primary Examiner — Bethany P Barham
Assistant Examiner — Dominic Lazardo
(74) Attorney, Agent, or Firm — Dilworth & Barrese, LLP (57) ABSTRACT Active ingredient capsules are proposed which are obtainable by, with the input of mechanical and thermal energy, (a) dissolving and/or dispersing proteins, polysaccharides and cellulose derivatives in water, (b) adding the active ingredients to be encapsulated, (c) hardening the resulting coacervates with the addition of tannins and optionally (d) then subjecting them to a spray drying.

12 Claims, 2 Drawing Sheets (51) Int. Cl.
  *A61K 8/65* (2006.01)
  *A61Q 11/00* (2006.01)
  *A61K 8/97* (2017.01)
  *A61K 9/68* (2006.01)
  *A61K 9/48* (2006.01)
  *A61K 9/50* (2006.01)
  *A23P 10/30* (2016.01)
  *A23L 33/10* (2016.01)
  *A23L 33/17* (2016.01)

(52) U.S. Cl.
  CPC ............ *A61K 8/65* (2013.01); *A61K 8/73* (2013.01); *A61K 8/731* (2013.01); *A61K 8/97* (2013.01); *A61K 9/0058* (2013.01); *A61K 9/4825* (2013.01); *A61K 9/5036* (2013.01); *A61K 9/5047* (2013.01); *A61K 9/5057* (2013.01); *A61Q 11/00* (2013.01); *A23V 2002/00* (2013.01); *A61K 2800/56* (2013.01)

(56) References Cited

U.S. PATENT DOCUMENTS

| | | | | |
|---|---|---|---|---|
| 4,946,624 A | * | 8/1990 | Michael | C11D 1/62 428/402.2 |
| 6,099,858 A | * | 8/2000 | Morton | A61K 8/11 264/4.1 |
| 7,335,631 B2 | * | 2/2008 | McDermott | A61K 8/11 512/1 |
| 2004/0151778 A1 | | 8/2004 | Joel et al. | |
| 2005/0079215 A1 | * | 4/2005 | Schleifenbaum | A61J 3/07 424/456 |
| 2009/0189304 A1 | * | 7/2009 | Friedmann | B01J 13/10 264/4.1 |
| 2010/0327216 A1 | * | 12/2010 | Jung | C09B 67/0013 252/70 |
| 2012/0148644 A1 | * | 6/2012 | Popplewell | A61K 8/11 424/401 |

FOREIGN PATENT DOCUMENTS

GB 1483542 A 8/1977
WO 02/064246 A1 8/2002

OTHER PUBLICATIONS de Kruif et al. "Complex coacertation of proteins and anionic polysaccharides," Current Opinion in Colloid & Interface Science vol. 9, No. 5, Dec. 1, 2004, pp. 340-349.

* cited by examiner

ACTIVE INGREDIENT CAPSULES

FIELD OF INVENTION

The invention is in the field of food technology and relates to novel water-insoluble capsules which are obtained using proteins, polysaccharides, cellulose derivates and tannins and release the active ingredients present therein in a delayed manner, to a process for producing the capsules, and to special uses of the cellulose derivatives and of the tannins in the course of the production process.

PRIOR ART

For a large number of applications, ranging from pharmacy via cosmetics, detergents and cleaners to fertilizers, the delayed release of active ingredients from a capsule shell has increasingly gained importance in recent years. In the food sector as well, it is often desirable if in particular flavourings are not spontaneously released upon incorporation into water or upon chewing, but are released in a time-delayed manner ("controlled release").

Besides macroscopic products with diameters in the range ranging to 1 cm, so-called microcapsules in particular are of interest. These are understood by the person skilled in the art as meaning spherical aggregates with a diameter in the range from about 0.0001 to about 5 and preferably 0.005 to 0.5 mm which contain at least one solid or liquid core which is surrounded by at least one continuous shell. More precisely, they are finely dispersed liquid or solid phases surrounded by film-forming polymers, during the production of which the polymers are deposited, following emulsification and coacervation or interfacial polymerization, on the material to be encased.

The shell of such microcapsules can consist of natural, semisynthetic or synthetic materials.

Natural shell materials are, for example, gum arabic, agar agar, agarose, maltodextrins, alginic acid or its salts, e.g. sodium or calcium alginate, fats and fatty acids, cetyl alcohol, collagen, chitosan, lecithins, gelatine, albumin, shellac, polysaccharides, such as starch or dextran, polypeptides, protein hydrolysates, sucrose and waxes.

Semisynthetic shell materials are inter alia chemically modified celluloses, in particular cellulose esters and ethers, e.g. cellulose acetate, ethylcellulose, hydroxypropylcellulose, hydroxypropylmethylcellulose and carboxymethylcellulose, and also starch derivatives, in particular starch ethers and esters. Synthetic shell materials are for example polymers such as polyacrylates, polyamides, polyvinyl alcohol or polyvinylpyrrolidone.

The encapsulation of active ingredients using gelatine and polysaccharides, specifically gum arabic, is the subject of numerous protective rights. The oldest documents originate from 1958 to 1974, namely U.S. Pat. No. 3,041,288; JP 50 027826 A and JP 51 013387 A.

U.S. Pat. No. 4,376,113 A (ROUSSEL UCLAF) refers to a process for making stable suspensions or powders of stable micro-capsules, according to which an o/w emulsion comprising colloidal gelatine, gum arabic and ethylhydroxyethylcellulose is subjected to coazervation by adjusting the pH value of the composition to 4.2 to 4.4, cross-linking the capsules by means of glutaric aldehyde and tannin, and immobilising the capsules thus obtained on a solid carrier.

European Patent application EP 0038985 A1 (BAYER) refers to micro-capsules with a shell obtained inter alia from tannins reaction products of gelatine and carbonyl compounds, and optionally gum arabic, carboxymethylcellulose and/or anionic polymers.

US patent application US 2004 0151778 AA (MAINELAB) covers a process for obtaining micro-capsules by coazervation of a soluble protein and a polyectrolyte.

British patent application GB 1483542 A (FUJI) discloses another process for making micro-capsules obtained from coazervation of gelatine, gum Arabic and at least one natural polymer.

International patent application WO 2002 064246 A1 (HAARMANN & REIMER) is related to a process for making blue micro-capsules using gelatine an gum Arabic as the main encapsulation agents.

Examples of microcapsules of the prior art are the following commercial products (in each case the shell material is given in brackets): Hallcrest Microcapsules (gelatine, gum arabic), Coletica Thalaspheres (maritime collagen), Lipotec Millicapseln (alginic acid, agar agar), Induchem Unispheres (lactose, microcrystalline cellulose, Hydroxypropyl-methylcellulose); Unicerin C30 (lactose, microcrystalline cellulose, Hydroxypropyl-methylcellulose), Kobo Glycospheres (modified starch, fatty acid esters, phospholipids), Softspheres (modified agar agar) and Kuhs Probiol Nanospheres (phospholipids), and Primaspheres and Primasponges (chitosan, alginates) and Primasys (phospholipids).

However, all of the classic encapsulation processes in the food sector are water-based and thus produce only water-soluble particles. However, since virtually all foods contain water, the customary technologies, such as e.g. spray drying, spray granulation or extrusion, achieve the required release upon heating the food or upon consumption only to a very limited extent, if at all.

Consequently, a first object of the invention consisted in providing water-insoluble particle with the highest possible active ingredient content and a D50 value of preferably about 10 to about 150 μm which release the active ingredient only upon food preparation or consumption.

A further aspect when producing microcapsules consists in the fact that, directly after their production, the products do not have adequate mechanical strength, but easily break up. For this purpose, the capsules are subjected to a hardening, whether by forming water-insoluble calcium salts on the shell or by means of crosslinking reactions with aldehydes, such as, for example, formaldehyde or glutaraldehyde. The use of such crosslinkers, however, is undesired for toxicological reasons, meaning that a further part object of the invention consisted in additionally also developing microcapsules of the described type which contain an alternative crosslinker which is permissible under food laws and is adequately effective from a technical point of view.

A third aspect of the invention is directed to the circumstance that the production of microcapsules via the route of coacervation, hardening and optionally drying is extremely time-consuming and requires large amounts of water for the dispersion. By contrast, it is desirable to reduce the amounts of water and in particular to considerably shorten the production time.

DESCRIPTION OF THE INVENTION

A first subject matter of the invention relates to active ingredient capsules which are obtainable by, with the input of mechanical and thermal energy,
(a) dissolving and/or dispersing proteins, polysaccharides and cellulose derivatives,
(b) adding the active ingredients to be encapsulated,
(c) hardening the resulting coacervates by adding tannins and optionally
(d) then subjecting them to a spray drying
on condition that the hardening step takes place in the absence of glutaric aldehyde.

A second aspect of the invention is directed to a process for producing active ingredient capsules in which, with the input of mechanical and thermal energy,
(a) proteins, polysaccharides and cellulose derivatives are dissolved and/or dispersed in water,
(b) the active ingredients to be encapsulated are added,
(c) the resulting coacervates are hardened by adding tannins and optionally
(d) then subjected to a spray drying
on condition that the hardening step takes place in the absence of glutaric aldehyde.

Surprisingly, it has been found that with the help of the process according to the invention, it is possible to provide water-insoluble coacervates which have a D50 value of in particular about 10 to about 150 μm, specifically about 50 to about 100 μm, and can be freed from water without problem by spray drying. The coacervates can be laden with highly diverse active ingredients in large amounts and release these in noteworthy amounts in the aqueous medium only after hours, for which reason they are particularly suitable for certain applications—such as for example in the catering sector.

The particle size can be varied within wide limits according to the requirements placed on the target product and the release. If a relatively rapid release is desired, the particles can be made larger (D50 of about 100 μm) or smaller (D50<50 μm) for a longer release time by varying the process conditions of stirrer speed and temperature.

Moreover, the process according to the invention makes do with a considerably smaller amount of water and allows the capsules to be produced—including spray drying—within the maximum of 12 hours; conventional processes usually require twice this time.

With tannin, an alternative hardener or crosslinking agent has been found which is not only approved for the food sector, but gives the capsule shells a breaking strength as is otherwise known only from the treatment with formaldehyde or glutaraldehyde.

Coating Substances

The active ingredient capsules are true shell/core capsules which are formed by coacervation of the coating substances and thereby encase the active ingredient. The shell is formed from three components (a1), (a2) and (a3), where, in the actual sense, only a coacervation of the proteins with the polysaccharides arises, while the cellulose derivatives function as protective colloids which prevent the sticking together of the capsules. This is per se likewise a surprising finding since cellulose derivatives are otherwise more likely used for "sticking". By using the cellulose derivatives it is simultaneously possible to halve the amount of water—via which the agglomeration is otherwise prevented.

Proteins. Proteins (component a1) that can be used are gelatines of highly diverse origin, thus for example based on beef, pork, chicken or fish. Preferably, they have a gel strength in the range from about 100 to about 300 Bloom, preferably about 150 to about 290 Bloom and in particular about 220 to 260 Bloom.

The parameter here is the mass in grams which is needed by a probe with a diameter of 0.5 of an inch to deflect the surface of a 6.67% gelatin/water mixture to a depth of 4 millimeters without breaking it. The experiment is carried out under standardized conditions at exactly 10° C. with prior ageing of the gelatin for 17 hours.

Polysaccharides. Suitable coating substances of the polysaccharide type including the heteropolysaccharides (component a2) are, for example, pectins, xanthans (also xanthan gum), and mixtures thereof. Preferably, the coating substance used is gum arabic, for example of the type Acacia seyal. Gum arabic consists of colourless to brown, matt, brittle, odourless sections with a shiny fracture which dissolve in warm water to give a clear, viscous, sticky liquid that does not have much of a taste and gives a weakly acidic reaction. It is composed primarily of the acidic alkaline earth metal and alkali metal salts of arabic acid (polyarabic acid), which is understood as meaning a branched polysaccharide consisting of L-arabinose, D-galactose, L-rhamnose and D-glucuronic acid in the ratio 3:3:1:1.

Agaroses are also suitable as coating substances; these can be present in the form of the agar agar that can be obtained from red algae, together with up to 30% by weight of non-gel-forming agaropectins. The main constituent of agaroses is linear polysaccharides from D-galactose and 3,6-anhydro-L-galactose, which are alternately β1,3- and β1,4-glycosidically linked.

The polysaccharides preferably have a molecular weight in the range from 110 000 to 160 000 and are both colourless and tasteless. Furthermore, preference is given to those types which also form gels in 1% strength by weight aqueous solution which do not melt below 80° C. and already solidify again above 40° C.

Cellulose derivatives. Besides chemically non-modified cellulose, suitable cellulose derivatives (component a3) are in particular cellulose ethers and cellulose esters with degrees of substitution above 80, preferably above 90 and in particular above 99%. Particular preference is given to carboxymethylcelluloses which are approved according to E466 as food additive, such as, for example, the type Ceroga 4510 C (Brenntag).

Active Ingredients

The selection of active ingredients which are suitable for encapsulation is uncritical and essentially governed only according to what intended use should be pursued. These may be e.g. dyes since the invention, however, is primarily directed to foods, the active ingredients are preferably aromas, in particular those substances which are sufficiently lipophilic and water-insoluble and can therefore also be readily encapsulated in an aqueous medium.

Typical examples of aromas include: acetophenone, allyl capronate, alpha-ionone, beta-ionone, anisaldehyde, anisyl acetate, anisyl formate, benzaldehyde, benzothiazole, benzyl acetate, benzyl alcohol, benzyl benzoate, beta-ionone, butyl butyrate, butyl capronate, butylidenephthalide, carvone, camphene, caryophyllene, cineol, cinnamyl acetate, citral, citronellol, citronellal, citronellyl acetate, cyclohexyl acetate, cymene, damascone, decalactone, dihydrocoumarin, dimethyl anthranilate, dodecalactone, ethoxyethyl acetate, ethylbutyric acid, ethyl butyrate, ethyl caprinate, ethyl capronate, ethyl crotonate, ethylfuraneol, ethylguaiacol, ethyl isobutyrate, ethyl isovalerate, ethyl lactate, ethylmethyl butyrate, ethyl propionate, eucalyptol, eugenol, ethyl heptylate, 4-(p-hydroxyphenyl)-2-butanone, gamma-decalactone, geraniol, geranyl acetate, grapefruit aldehyde, methyl dihydrojasmonate (e.g. Hedion®), heliotropin, 2-heptanone, 3-heptanone, 4-heptanone, trans-2-heptenal, cis-4-heptenal, trans-2-hexenal, cis-3-hexenol, trans-2-hexenoic acid, trans-3-hexenoic acid, cis-2-hexenyl acetate, cis-3-hexenyl acetate, cis-3-hexenyl capronate, trans-2-hexenyl capronate, cis-3-hexenyl formate, cis-2-hexyl acetate, cis-3-hexyl acetate, trans-2-hexyl acetate, cis-3-hexyl formate, para-hydroxybenzylacetone, isoamyl alcohol, isoamyl isovalerate, isobutyl butyrate, isobutyraldehyde, isoeugenol methyl ether, isopropylmethylthiazole, lauric acid, levulinic acid, linalool, linalool oxide, linalyl acetate, menthol, menthofuran, methyl anthranilate, methylbutanol, methylbutyric acid, 2-methylbutyl acetate, methyl capronate, methyl cinnamate, 5-methylfurfural, 3,2,2-methylcyclopentenolone, 6,5,2-methylheptenone, methyl dihydrojasmonate, methyl jasmonate, 2-methylmethyl butyrate, 2-methyl-2-pentenolic acid, methyl thiobutyrate, 3,1-methylthiohexanol, 3-methylthiohexyl acetate, nerol, neryl acetate, trans,trans-2,4-nonadienal, 2,4-nonadienol, 2,6-nonadienol, 2,4-nonadienol, nootkatone, delta-octalactone, gamma octalactone, 2-octanol, 3-octanol, 1,3-octenol, 1-octyl acetate, 3-octyl acetate, palmitic acid, paraldehyde, phellandrene, pentanedione, phenylethyl acetate, phenylethyl alcohol, phenylethyl alcohol, phenylethyl isovalerate, piperonal, propionaldehyde, propyl butyrate, pulegone, pulegol, sinensal, sulfurol, terpine, terpineol, terpineol, 8,3-thiomenthanone, 4,4,2-thiomethylpentanone, thymol, delta-undecalactone, gamma-undecalactone, valencene, valeric acid, vanillin, acetoin, ethylvanillin, ethylvanillin isobutyrate (=3-ethoxy-4-isobutyryloxybenzaldehyde), 2,5-dimethyl-4-hydroxy-3 (2H)-furanone and modifications thereof (here preferably homofuraneol (=2-ethyl-4-hydroxy-5-methyl-3(2H)-furanone), homofuroneol (=2-ethyl-5-methyl-4-hydroxy-3(2H)-furanone and 5-ethyl-2-methyl-4-hydroxy-3(2H)-furanone), maltol and maltol modifications (here preferably ethylmaltol), coumarin and coumarin modifications, gamma-lactones (here preferably gamma-undecalactone, gamma-nonalactone, gamma-decalactone), delta-lactones (here preferably 4-methyldeltadecalactone, massoilactone, delta-decalactone, tuberolactone), methyl sorbate, divanillin, 4-hydroxy-2 (or 5)-ethyl-5 (or 2)-methyl-3(2H)furanone, 2-hydroxy-3-methyl-2-cyclopentenone, 3-hydroxy-4,5-dimethyl-2(5H)-furanone, acetic acid isoamyl ester, butyric acid ethyl esters, butyric acid n-butyl ester, butyric acid isoamyl ester, 3-methylbutyric acid ethyl ester, n-hexanoic acid ethyl ester, n-hexanoic acid allyl ester, n-hexanoic acid n-butyl ester, n-octanoic acid ethyl ester, ethyl 3-methyl-3-phenylglycidate, ethyl 2-trans-4-cis-decadienoate, 4-(p-hydroxyphenyl)-2-butanone, 1,1-dimethoxy-2,2,5-trimethyl-4-hexane, 2,6-dimethyl-5-hepten-1-al and phenylacetaldehyde, 2-methyl-3-(methylthio)furan, 2-methyl-3-furanthiol, bis(2-methyl-3-furyl)disulfide, furfurylmercaptan, methional, 2-acetyl-2-thiazoline, 3-mercapto-2-pentanone, 2,5-dimethyl-3-furanthiol, 2,4,5-trimethylthiazole, 2-acetylthiazole, 2,4-dimethyl-5-ethylthiazole, 2-acetyl-1-pyrroline, 2-methyl-3-ethylpyrazine, 2-ethyl-3,5-dimethylpyrazine, 2-ethyl-3,6-dimethylpyrazine, 2,3-diethyl-5-methylpyrazine, 3-isopropyl-2-methoxypyrazine, 3-isobutyl-2-methoxypyrazine, 2-acetylpyrazine, 2-pentylpyridine, (E,E)-2,4-decadienal, (E,E)-2,4-nonadienal, (E)-2-octenal, (E)-2-nonenal, 2-undecenal, 12-methyltridecanal, 1-penten-3-one, 4-hydroxy-2,5-dimethyl-3(2H)-furanone, guaiacol, 3-hydroxy-4,5-dimethyl-2(5H)-furanone, 3-hydroxy-4-methyl-5-ethyl-2(5H)-furanone, cinnamyl aldehyde, cinnamyl alcohol, methyl salicylate, isopulegol, and (here not explicitly specified) stereoisomers, enantiomers, positional isomers, diastereomers, cis/trans-isomers or epimers of these substances.

For applications in which the capsules are not consumed but come into contact with the oral mucosa, perfume oils can also be encapsulated.

Perfume oils that may be mentioned are mixtures of natural and synthetic fragrances. Natural fragrances are extracts from flowers (lily, lavender, rose, jasmine, neroli, ylang ylang), stems and leaves (geranium, patchouli, petitgrain), fruits (anise, coriander, caraway, juniper), fruit peels (bergamot, lemon, orange), roots (maize, angelica, celery, cardamom, costus, iris, calmus), woods (pinewood, sandalwood, guaiac wood, cedar wood, rosewood), herbs and grasses (tarragon, lemon grass, sage, thyme), needles and branches (spruce, fir, pine, dwarf-pine), resins and balsams (galbanum, elemi, benzoe, myrrh, olibanum, opoponax). Also of suitability are animal raw materials, such as, for example, civet and castoreum. Typical synthetic fragrance compounds are products of the ester, ether, aldehyde, ketone, alcohol and hydrocarbon types. Fragrance compounds of the ester type are e.g. benzyl acetate, phenoxyethyl isobutyrate, p-tert-butyl cyclohexylacetate, linalyl acetate, dimethyl benzyl carbinyl acetate, phenylethyl acetate, linalyl benzoate, benzyl formate, ethyl methylphenyl glycinate, allyl cyclohexylpropionate, styrallyl propionate and benzyl salicylate. The ethers include, for example, benzyl ethyl ethers, the aldehydes include e.g. the linear alkanals having 8 to 18 carbon atoms, citral, citronellal, citronellyloxyacetaldehyde, cyclamenaldehyde, hydroxycitronellal, lilial and bourgeonal, the ketones include e.g. the ionones, α-isomethylionone and methyl cedryl ketone, the alcohols include anethole, citronellol, eugenol, isoeugenol, geraniol, linalool, phenylethyl alcohol and terpineol, the hydrocarbons include primarily the terpenes and balsams. However, preference is given to using mixtures of different fragrances which together produce a pleasant scent note. Essential oils of lower volatility, which are mostly used as aroma components, are also suitable as perfume oils, e.g. sage oils, Camilla oil, clove oil, Melissa oil, mint oil, cinnamon leaf oil, linden blossom oil, juniper berry oil, vetiver oil, olibanum oil, galbanum oil, labolanum oil and lavandin oil. Preference is given to using bergamot oil, dihydromyrcenol, lilia, lyral, citronellol, phenylethyl alcohol, α-hexylcinnamaldehyde, geraniol, benzyl acetone, cyclamenaldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, vertofix Coeur, iso-E-Super, Fixolide NP, evernyl, iraldein gamma, phenylacetic acid, geranyl acetate, benzyl acetate, rose oxide, romillat, irotyl and floramat alone or in mixtures.

Suitable aromas are, for example, peppermint oil, spearmint oil, anise oil, star anise oil, caraway oil, eucalyptus oil, fennel oil, lemon oil, wintergreen oil, clove oil, menthol and the like.

Coacervation

The encapsulation reaction is a coacervation between the proteins and the polysaccharides, preferably gelatine and gum arabic, in which the cellulose derivative serves merely as protective colloid and prevents agglomeration of the freshly formed capsules.

Preferably, the components (a1), (a2), and (a3) are used in the weight ratio of about 10:(1 to 5):(0.5 to 2) and in particular 10:(2 to 4):(1 to 1.5). The coacervation takes place with the input of mechanical and thermal energy, i.e. during the preparation the reaction mixture is stirred and adjusted to a temperature in the range from about 10 to about 90° C. In this connection, it has proven to be advantageous to start the coacervation of the coating substances at temperatures in the range from about 50 to about 90 at gentle stirring power and then to add the active ingredients, which automatically leads to a cooling of the reaction mixture to about 40° C. However, it is advisable to increase the stirring power and to cool the mixture in steps to about 10° C. Here, it is the case that with greater stirring power and longer reaction time smaller capsules are formed, and vice versa. Suitable further additives here are physiologically compatible acids, such as acetic acid, citric acid or lactic acid, with which the pH of the solution is kept in the acidic range at about 3 to 5. Since the mixtures have a tendency to develop foam, it is likewise recommended to add antifoams, for example standard commercial silicone antifoams.

Hardening or Crosslinking

After the coacervation, the capsules still have a flexible shell which does not have any special stability and therefore breaks easily. For this purpose, a hardening or crosslinking of the shell is carried out. For this purpose, natural plant tanning substances of the tannin type are used which, from a chemical point of view, are proanthocyanidins, as can be found in dicotyledonus shrubs, bushes and leaves particularly in the tropics and subtropics. The terpenes generally have molecular weights in the range from 500 to 3000 kDa.

A preferred example of a suitable tannin is corigallin, a bridged 1,3,5-trigalloyltannin of the following formula:

Tannins are classified according to whether they are hydrolysable or not. The former can be degraded to give glucose, other polyhydric alcohols, gallic acid or ellagic acid. Condensed tannins, on the other hand, consist of flavonoid phenols polymerized with one another, such as catechin, epicatechin or anthocyanins.

For the hardening, an aqueous preparation of the tannins is added to the aqueous dispersion containing the crude capsules and stirred at about 10 to about 20° C. for about 5 to about 10 h. Usually, the tannins are added in amounts of from about 0.1 to about 2% by weight and preferably from about 0.5 to about 1.5% by weight—based on the coacervates.

Spray Drying

After the coacervation and hardening, the capsules according to the invention are present as a dispersion in water. In this form, they are fundamentally already marketable, although, for the purposes of preservation, it is recommended to dry them. Of suitability in principle for this purpose are methods such as lyophilisation, although preference is given to spray drying for example in the fluidized bed. In this connection, it has proven to be advantageous to add further polysaccharides, preferably dextrins and in particular maltrodextrins to the dispersion at temperatures of from about 20 to about 50° C. and preferably about 40° C.; these assist the drying process and protect the capsules during this operation. Here, the amount of polysaccharides used can be about 50 to about 150% by weight and preferably about 80 to about 120% by weight, based on the capsule mass in the dispersion.

The spray drying itself can be carried out continuously or batch-wise in conventional spray apparatuses, in which case the inlet temperature is about 170 to about 200° C. and preferably about 180 to 185° C., and the exit temperature is about 70 to about 80° C. and preferably about 72 to 78° C.

INDUSTRIAL APPLICABILITY

A further subject matter of the present patent application is directed to preparations for oral administration which comprise the active ingredient capsules according to the invention, for example in amounts of from 0.1 to about 10% by weight, preferably about 1 to about 8% by weight and in particular about 2 to about 5% by weight.

Preparations for oral administration are to be understood primarily as meaning foods and luxuries. Likewise encompassed, however, are also those preparations which, although they come into contact with oral mucosa, are not intended for consumption. These include mouth and dental care compositions and chewing gums.

Foods

The foods are preferably baked goods, for example bread, dry biscuits, cakes, other pastries, confectionery (for example chocolate, chocolate bar products, other bar products, fruit gums, hard and soft caramels, chewing gum), alcoholic or non-alcoholic drinks (for example coffee, tea, ice tea, wine, wine-based drinks, beer, beer-based drinks, liqueurs, spirits, brandies, (carbonated) fruit-based soft drinks, (carbonated) isotonic drinks, (carbonated) refreshing drinks, nectars, spritzers, and vegetable juices, fruit or vegetable juice preparations, instant drinks (for example instant chocolate drinks), instant tea drinks, instant coffee drinks, instant fruit drinks), meat products (for example ham, cured or uncured sausage preparations, spiced or marinated fresh or salted meat products), eggs or egg products (dried egg, egg white, egg yolk), cereal products (for example breakfast cereals, muesli bars, pre-fermented prepared rice products), dairy products (for example milk drinks, buttermilk drinks, ice cream, yoghurt, kefir, cream cheese, soft cheese, hard cheese, dried milk powder, whey, whey drinks, butter, buttermilk, partially or completely hydrolysed milk protein-containing products), products made from soy protein or other soybean fractions (for example soya milk and products made therefrom, fruit drinks containing soya protein, soya lecithin-containing preparations, fermented products such as tofu or tempeh or products made therefrom), products made of other plant protein sauces, for example oat protein drinks, fruit preparations (for example jams, fruit sorbets, fruit sauces, fruit fillings), vegetable preparations (for example ketchup, sauces, dried vegetables, frozen vegetables, prefermented vegetables, preserved vegetables), snacks (for example baked or fried potato crisps or potato dough products, extrudants based on maize or peanuts), products based on fats and oils or emulsions thereof (for example mayonnaise, remoulade, dressings), other ready meals and soups (for example dried soups, instant soups, preformented soups), spices, spice mixes, and in particular seasonings, which are used for example in the snacks sector.

These foods can have further ingredients, such as, for example:

Sweeteners. Suitable sweeteners or sweet-tasting additives are firstly carbohydrates and specifically sugars, such as for example sucrose/saccharose, trehalose, lactose, maltose, melizitose, raffinose, palatinose, lactulose, D-fructose, D-glucose, D-galactose, L-rhamnose, D-sorbose, D-mannose, D-tagatose, D-arabinose, L-arabinose, D-ribose, D-glyceraldehyde, or maltodextrin. Likewise of suitability are plant preparations which comprise these substances, for example based on sugar beet (Beta vulgaris ssp., sugar fractions, sugar syrup, molasses), sugar cane (Saccharum officinarum ssp., molasses, sugar cane syrup), maple syrup (Acer ssp.) or agave (agave thick juice).

Also of suitability are
- synthetic, i.e. generally enzymatically prepared, starch or sugar hydrolysates (invert sugar, fructose syrup);
- fruit concentrates (e.g. based on apples or pears);
- sugar alcohols (e.g. erythritol, threitol, arabitol, ribotol, xylitol, sorbitol, mannitol, dulcitol, lactitol);
- proteins (e.g. miraculin, monellin, thaumatin, curculin, brazzein);
- sweeteners (e.g. magap, sodium cyclamate, acesulfame K, neohesperidin dihydrochalcone, saccharin sodium salt, aspartame, super aspartame, neotame, alitame, sucralose, stevioside, rebaudioside, lugduname, carrelame, sucrononate, sucrooctate, monatin, phenylodulcin);
- sweet-tasting amino acids (e.g. glycine, D-leucine, D-threonine, D-asparagine, D-phenylalanine, D-tryptophan, L-proline);
- further sweet-tasting low molecular weight substances, such as e.g. hernandulcin, dihydrochalcone glycosides, glycyrrhizine, glycerrhetic acid, its derivatives and salts, extracts of licorice (Glycyrrhizza glabra ssp.), Lippia dulcis extracts, Momordica ssp. extracts or
- individual substances such as e.g. Momordica grosvenori [Luo Han Guo] and the mogrosides obtained therefrom, Hydrangea dulcis or Stevia ssp. (e.g. Stevia rebaudiana) extracts.

Food acids. The foods can contain carboxylic acids. Acids for the purposes of the invention are preferably acids permissible in foods, and salts thereof, in particular those specified here:

E 260—Acetic acid
E 270—Lactic acid
E 290—Carbon dioxide
E 296—Malic acid
E 297—Fumaric acid
E 330—Citric acid
E 331—Sodium citrate
E 332—Potassium citrate
E 333—Calcium citrate
E 334—Tartaric acid
E 335—Sodium tartrate
E 336—Potassium tartrate
E 337—Sodium/potassium tartrate
E 338—Phosphoric acid
E 353—Metatartaric acid
E 354—Calcium tartrate
E 355—Adipic acid
E 363—Succinic acid
E 380—Triammonium citrate
E 513—Sulphuric acid
E 574—Gluconic acid
E 575—Glucono-delta-lactone Acid regulators. Regulators are food additives which keep the acidity or the basicity and therefore the desired pH of the food constant. They are mostly organic acids and their salts, carbonates, more rarely also inorganic acids and salts thereof. The addition of an acid regulator increases in part the stability and solidity of the food, brings about a desired precipitation and improves the effect of preservatives. In contrast to acidifiers, they are not used to change the taste of foods. Their effect is based on the formulation of a buffer system in the food where the pH only changes slightly, if at all, upon addition of acidic or basic substances. Examples are:

E 170—Calcium carbonate
E 260-263—Acetic acid and acetates
E 270—Lactic acid
E 296—Malic acid
E 297—Fumaric acid
E 325-327—Lactates (lactic acid)
E 330-333—Citric acid and citrates
E 334-337—Tartaric acid and tartrates
E 339-341—Orthophosphates
E 350-352—Malates (malic acid)
E 450-452—Di-, tri- and polyphosphates
E 500-504—Carbonates (carbonic acid)
E 507—Hydrochloric acid and chlorides
E 513-517 Sulphuric acid and sulphates
E 524-528—Hydroxides
E 529-530—Oxides
E 355-357—Adipic acid and adipates
E 574-578—Gluconic acid and gluconates Thickeners. Thickeners are substances which are primarily able to bind water. Withdrawing nonbound water leads to an increase in the viscosity. Above a concentration that is characteristic for each thickener, as well as this effect, network effects also arise which lead to a mostly overproportional increase in the viscosity. In this case, it can be said the molecules "communicate" with one another, i.e. become entangled. Most thickeners are linear or branched macromolecules (e.g. polysaccharides or proteins), which can interact with one another as a result of intermolecular interactions, such as hydrogen bridges, hydrophobic interactions or ionic bonds. Extreme cases of thickeners are sheet silicates (bentonites, hectorites) or hydrated $SiO_2$ particles which can be present dispersed as particles and bind water in their solid-like structure and/or can interact with one another on account of the described interactions. Examples are:

E 400—Alginic acid
E 401—Sodium alginate
E 402—Potassium alginate
E 403—Ammonium alginate
E 404—Calcium alginate
E 405—Propylene glycol alginate
E 406—Agar Agar
E 407—Carrageenan, furcelleran
E 407—Carob seed flour
E 412—Guar seed flour
E 413—Tragacanth
E 414—Gum arabic
E 415—Xanthan
E 416—Karaya (Indian Traganth)
E 417—Tara corn flour (Peruvian carob seed flour)
E 418—Gellan
E 440—Pectin, opekta
E 440ii—Amidated pectin
E 460—Microcrystalline cellulose, cellulose powder
E 461—Methylcellulose E 462—Ethylcellulose
E 463—Hydroxypropylcellulose
E 465—Methylethylcellulose
E 466—Carboxymethylcellulose, sodium carboxymethylcellulose Reducing agents. The foods can furthermore also have reducing agents. Reducing agents in the context of the invention are preferably reducing agents that are permissible in foods, in particular those specified here:
E 220—Sulphur dioxide
E 221—Sodium sulphite
E 222—Sodium hydrogensulphite
E 223—Sodium disulphite
E 224—Potassium disulphite
E 226—Calcium sulphite
E 227—Calcium hydrogensulphite
E 228—Potassium hydrogensulphite
E 300—Ascorbic acid
E 301—Sodium L-ascorbate
E 302—Calcium L-ascorbate
E 304—Ascorbic acid ester
E 306—Tocopherol
E 307—Alpha-tocopherol
E 308—Gamma-tocopherol
E 309—Delta-tocopherol
E 310—Propyl gallate
E 311—Octyl gallate
E 312—Dodecyl gallate
E 315—Isoascorbic acid
E 316—Sodium isoascorbate
E 319—tert-Butylhydroquinone (TBHQ)
E 320—Butylhydroxyanisole
E 321—Butylhydroxytoluene
E 322—Lecithin
E 330—Citric acid
E 512—Tin II chloride Oral and Dental Care Compositions Oral preparations according to the invention can also serve for oral and dental cleaning and care. Examples thereof are toothpastes, dental gels, dental powders, mouthwashes and the like. Toothpastes or dental creams are generally understood as meaning gel-like or pasty preparations made from water, thickeners, humectants, abrasive or cleaning bodies, surfactants, sweeteners, aroma substances, deodorizing active ingredients, as well as active ingredients to combat oral and dental diseases. All customary cleaning bodies, such as e.g. chalk, dicalcium phosphate, insoluble sodium metaphosphate, aluminium silicates, calcium pyrophosphate, finely divided synthetic resins, silicas, aluminium oxide and aluminium oxide trihydrate can be used in the toothpastes according to the invention.

Preferably suitable cleaning bodies for the toothpastes according to the invention are primarily finely divided xerogel silicas, hydrogel silicas, precipitated silicas, aluminium oxide trihydrate and finely divided alpha-aluminium oxide or mixtures of these cleaning bodies in amounts of from 15 to 40% by weight of the toothpaste. Suitable humectants are predominantly low molecular weight polyethylene glycols, glycerol, sorbitol or mixtures of these products in amounts up to 50% by weight. Among the known thickeners, the thickening, finely divided gel silicas and hydrocolloids, such as e.g. carboxymethylcellulose, hydroxyethylcellulose, hydroxypropyl guar, hydroxyethyl starch, polyvinylpyrrolidone, high molecular weight polyethylene glycol, plant gums such as tragacanth, agar agar, carrageenan moss, gum arabic, xanthan gum and carboxyvinyl polymers (e.g. Carbopol® grades) are suitable. In addition to the mixtures of menthofuran and menthol compounds, the oral and dental care compositions can in particular comprise surface-active substances, preferably anionic and nonionic high-foaming surfactants, such as the substances already listed above, but in particular alkyl ether sulphate salts, alkyl polyglucosides and mixtures thereof.

Further customary toothpaste additives are:
Preservatives and antimicrobial substances such as e.g. p-hydroxybenzoic acid methyl, ethyl or propyl ester, sodium sorbate, sodium benzoate, bromochlorophen, phenylsalicylic acid esters, thymol and the like;
Anti-tartar active ingredients, e.g. organophosphates such as 1-hydroxyethane-1.1-diphosphonic acid, 1-phosphonopropane-1,2,3-tricarboxylic acid and others, which are known e.g. from U.S. Pat. No. 3,488,419, DE 2224430 A1 and DE 2343196 A1;
Other caries-inhibiting substances such as e.g. sodium fluoride, sodium monofluorophosphate, tin fluoride;
Sweeteners, such as e.g. saccharin-sodium, sodium cyclamate, sucrose, lactose, maltose, fructose or Apartam®, (L-aspartyl-Lphenylalanine methyl ester), Stevia extracts or sweetening constituents thereof, in particular Rebaudioside;
Additional aromas such as e.g. eucalyptus oil, anise oil, fennel oil, caraway oil, methyl acetate, cimaldehyde, anethol, vanillin, thymol, and mixtures of these and other natural and synthetic aromas;
Pigments such as e.g. titanium dioxide;
Dyes;
Buffer substances such as e.g. primary, secondary or tertiary alkali metal phosphates or citric acid/sodium citrate;
Wound-healing and anti-inflammatory substances such as e.g. allantoin, urea, azulene, chamomile active ingredients and acetylsalicylic acid derivatives.

A preferred embodiment of the cosmetic preparations is toothpastes in the form of an aqueous, pasty dispersion, comprising polishing agents, humectants, viscosity regulators and optionally further customary components, and also the mixture of menthofuran and menthol compounds in amounts of from 0.5 to 2% by weight.

In mouthwashes, a combination with aqueous-alcoholic solutions of varying concentration gradient of essential oils, emulsifiers, astringent and toning drug extracts, tartar-preventing, antibacterial additives and taste correctives is directly possible. A preferred embodiment of the invention is a mouthwash in the form of an aqueous or aqueous-alcoholic solution comprising the mixture of menthofuran and menthol compounds in amounts of from 0.5 to 2% by weight. In mouthwashes which are diluted prior to use, adequate effects can be achieved with higher concentrations corresponding to the envisaged dilution ratio.

To improve the flow behaviour, hydrotropes, such as, for example, ethanol, isopropyl alcohol, or polyols can also be used; these substances largely correspond to the carriers described at the start. Polyols which are suitable here preferably have 2 to 15 carbon atoms and at least two hydroxyl groups. The polyols can also contain further functional groups, in particular amino groups, and/or be modified with nitrogen. Typical examples are
glycerol;
alkylene glycols, such as, for example, ethylene glycol, diethylene glycol, propylene glycol, butylene glycol, hexylene glycol, and polyethylene glycols with an average molecular weight of from 100 to 1000 daltons;
technical-grade oligoglycerol mixtures with a degree of self-condensation of from 1.5 to 10, such as for example technical-grade diglycerol mixtures with a diglycerol content of from 40 to 50% by weight;

methylol compounds, such as in particular trimethylolethane, trimethylolpropane, trimethylolbutane, pentaerythritol and dipentaerythritol;

low alkyl glycosides, in particular those having 1 to 8 carbon atoms in the alkyl radical, such as for example methyl and butyl glycoside;

sugar alcohols having 5 to 12 carbon atoms, such as for example sorbitol or mannitol, sugars having 5 to 12 carbon atoms, such as for example glucose or sucrose;

amino sugars, such as for example glucamine;

dialcoholamines, such as diethanolamine or 2-amino-1,3-propanediol.

Suitable preservatives are, for example, phenoxyethanol, formaldehyde solution, parabens, pentanediol or sorbic acid, and the silver complexes known under the name Surfacine® and the other classes of substance listed in Annex 6, Part A and B of the Cosmetics Ordinance. The preparations can furthermore also comprise perfume oils, which are preferably present in encapsulated form in the context of the invention. Suitable examples have already been mentioned above.

Chewing Gums

Finally, the oral preparations may also be chewing gums. These products typically comprise one water-insoluble component and one water-soluble component.

The water-insoluble base, which is also referred to as "gum base", usually comprises natural or synthetic elastomers, resins, fats and oils, plasticizers, fillers, dyes, and optionally waxes. The fraction of the base in the overall composition usually constitutes 5 to 95, preferably 10 to 50 and in particular 20 to 35% by weight. In a typical embodiment of the invention, the base is composed of 20 to 60% by weight of synthetic elastomers, 0 to 30% by weight of natural elastomers, 5 to 55% by weight of plasticizers, 4 to 35% by weight of fillers and, in minor amounts, additives such as dyes, antioxidants and the like, with the proviso that they are at most water-soluble in small amounts.

Suitable synthetic elastomers are, for example, polyisobutylenes with average molecular weights (according to GPC) of from 10 000 to 100 000 and preferably 50 000 to 80 000, isobutylene-isoprene copolymers ("butyl elastomers"), styrene-butadiene copolymers (styrene: butadiene ratio e.g. 1:3 to 3:1), polyvinyl acetates with average molecular weights (according to GPC) of from 2000 to 90 000 and preferably 10 000 to 65 000, polyisoprenes, polyethylene, vinyl acetate-vinyl laurate copolymers and mixtures thereof. Examples of suitable natural elastomers are rubbers such as smoked or liquid Latex or guayule and natural gum substances such as jelutong, lechi caspi, perillo, sorva, massaranduba balata, massaranduba chocolate, nispero, rosindinba, chicle, gutta hang kang, and mixtures thereof. The selection of synthetic and natural elastomers and mixing ratios thereof is essentially governed by whether bubbles should be produced with the chewing gums ("bubble gums") or not. Preference is given to using elastomer mixtures which comprise jelutong, chicle, sorva and massaranduba.

In most cases, the elastomers have proven to be too hard or not very mouldable during processing, meaning that it has proven to be advantageous to co-use special plasticizers, which naturally have to satisfy in particular also all of the requirements placed on the approval as food additives. Of suitability in this regard are in particular esters of resin acids, for example esters of low aliphatic alcohols or polyols with completely or partially hydrogenated, monomeric or oligomeric resin acids. In particular, the methyl, glycerol, or pentareythritol esters, and mixtures thereof are used for this purpose. Alternatively, terpene resins are also suitable which can be derived from alpha-pinene, beta-pinene, delta-limonene or mixtures thereof.

Suitable fillers or texturizers are magnesium carbonate or calcium carbonate, ground pumice, silicates, specifically magnesium silicates or aluminium silicates, clays, aluminium oxides, talc, titanium dioxide, mono-, di- and tri-calcium phosphate, and cellulose polymers.

Suitable emulsifiers are tallow, hydrogenated tallow, hydrogenated or partially hydrogenated vegetable oils, cocoa butter, partial glycerides, lecithin, triacetin and saturated or unsaturated fatty acids having 6 to 22 and preferably 12 to 18 carbon atoms, and mixtures thereof.

Suitable dyes and whiteners are, for example, the FD and C types approved for colouring foods, plant and fruit extracts, and also titanium dioxide.

The base masses can comprise waxes or be wax-free; examples of wax-free compositions can be found inter alia in the patent specification U.S. Pat. No. 5,286,500, to the contents of which reference is hereby expressly made.

In addition to the water-insoluble gum base, chewing gum preparations regularly comprise a water-soluble fraction which is formed for example of softeners, sweeteners, fillers, flavourings, flavour enhancers, emulsifiers, dyes, acidifiers, antioxidants and the like, here with the proviso that the constituents have an at least adequate solubility in water. Depending on the solubility in water of the specific representatives, individual constituents can accordingly belong either to the water-insoluble phase or to the water-soluble phase. However, it is also possible to use combinations for example of a water-soluble and a water-insoluble emulsifier, in which case the individual representatives are then found in different phases. Usually, the water-insoluble fraction constitutes 5 to 95 and preferably 20 to 80% by weight of the preparation.

Water-soluble softeners or plasticizers are added to the chewing gum compositions in order to improve the chewability and the chewing feel and are present in the mixtures typically in amounts of from 0.5 to 15% by weight. Typical examples are glycerol, lecithin, and aqueous solutions of sorbitol, hydrogenated starch hydrolysates or corn syrup.

Suitable sweeteners are either sugar-containing or sugar-free compounds, which are used in amounts of from 5 to 95, preferably 20 to 80 and in particular 30 to 60% by weight, based on the chewing gum composition. Typical saccharide sweeteners are sucrose, dextrose, maltose, dextrin, dried inverted sugar, fructose, levulose, galactose, corn syrup, and mixtures thereof. Suitable sugar substitutes are sorbitol, mannitol, xylitol, hydrogenated starch hydrolysates, maltitol and mixtures thereof. Furthermore of suitability as additives are also so-called HIAS ("High Intensity Artificial Sweeteners"), such as, for example, sucralose, aspartame, acesulphame salts, alitame, saccharin and saccharin salts, cyclamic acid and salts thereof, glycyrrhizins, dihydrochalcones, thaumatin, monellin and the like, alone or in mixtures. Of particular effectiveness are also the hydrophobic HIAS, the subject matter of the International Patent Application WO 2002 091849 A1 (Wrigleys), and stevia extracts and active constituents thereof, in particular rebaudioside A. The use amount of these substances depends primarily on their performance and is typically in the range from 0.02 to 8% by weight.

Of particular suitability for producing low-calorie chewing gums are fillers such as, for example, polydextrose, raftilose, rafitilin, fructooligosaccharides (NutraFlora), palatinose oligosaccharides, guar gum hydrolysate (Sun Fiber), and dextrins.

The selection of further flavourings preferably encapsulated in the context of the invention is practically unlimited and unimportant for the essence of the invention. Usually, the total fraction of all flavourings is 0.1 to 15 and preferably 0.2 to 5% by weight, based on the chewing gum composition. Suitable further flavourings are for example essential oils, synthetic aromas and the like, such as for example anise oil, star anise oil, caraway oil, eucalyptus oil, fennel oil, lemon oil, wintergreen oil, clove oil, and the like, as are also used for example in oral and dental care compositions.

The chewing gums can furthermore comprise auxiliaries and additives which are suitable for example for dental care, specifically for controlling plaque and gingivitis, such as e.g. chlorhexidine, CPC or trichlosan. Furthermore, pH regulators (e.g. buffers or urea), active ingredients to combat caries (e.g. phosphates or fluorides), biogenic active ingredients (antibodies, enzymes, caffeine, plant extracts) can be present provided these substances are approved for foods and do not interact with one another in an undesired way.

A further subject of the present invention covers the use of cellulose derivatives, in particular of carboxymethylcelluloses as protective colloids in the production of active ingredient capsules with a shell made of proteins and/or polysaccharides A last subject matter of the invention relates to the use of the active ingredient capsules according to the invention for producing preparations for oral administration.

EXAMPLES

Preparation Examples and Examples Relating to Application Technology

Example 1

Preparation of an Encapsulated Citrus Aroma

In a stirred tank, 350 kg of water (drinking water quality) were introduced and heated to 80° C. at about 40% of the stirrer power. Then, 2.4 kg of gum arabic (Seyal type), 1.8 kg of carboxymethylcellulose (Ceroga 4510C, Röper), and 11.8 kg of beef gelatine (240 Bloom) were added and the mixture was stirred for 45 min. Then, it was cooled to 55° C. and 115 kg of citrus aroma were added, whereupon the temperature cooled to about 42° C. By adding 1.2 kg of acetic acid, the pH was adjusted to 4.2 and, in order to avoid foam, 0.4 kg of a standard commercial silicone antifoam was added. The stirrer speed was increased to 75% and the tank contents were slowly cooled from 40° C. to about 10° C. over the course of 2 h. Upon reaching 20° C., the stirring power was reduced to 40%. Finally, at 10° C., a preparation of 1.4 kg of tannin in 5 l of water was slowly added. Cooling was switched off and the mixture was stirred for a further 8 h. The capsules formed had a D50 of about 50 μm.

Example 2

Spray Drying of the Capsules 484 kg of the aqueous capsule dispersion from Example 1 were heated to 40° C. in a tank with stirring and slowly mixed with 115 kg of wheat-based maltodextrin. Then, the mixture was added via a spray tower. The inlet temperature was 180 to 185° C., the exit temperature 72 to 78° C.

Example 3

Controlled Release of the Active Ingredients from the Capsules

The capsules according to the invention are not water-soluble, which leads to them only releasing the contained active ingredient in a delayed manner in an aqueous environment. For this purpose, Examples 1 and 2 were repeated, except the aroma substance was exchanged in the same weight for neutral which had been admixed with a blue dye. The capsules were then dispersed in a colourless neutral oil and the release of the dye from the capsules, i.e. the colouration of the neutral oil, was monitored over time using a Lab colour measurement system. The results are summarized in Table 1.

TABLE 1

| Controlled release of blue dye | |
|---|---|
| Time [min] | Relative colour intensity [%] |
| 1 | 29 |
| 2 | 30 |
| 3 | 31 |
| 4 | 35 |
| 5 | 37 |
| 15 | 41 |
| 30 | 43 |
| 45 | 52 |
| 60 | 55 |
| 120 | 67 |
| 180 | 80 |
| 1200 | 95 |

Example 4

Colour Release upon Shearing and at Relatively High Temperatures

Figure 1:
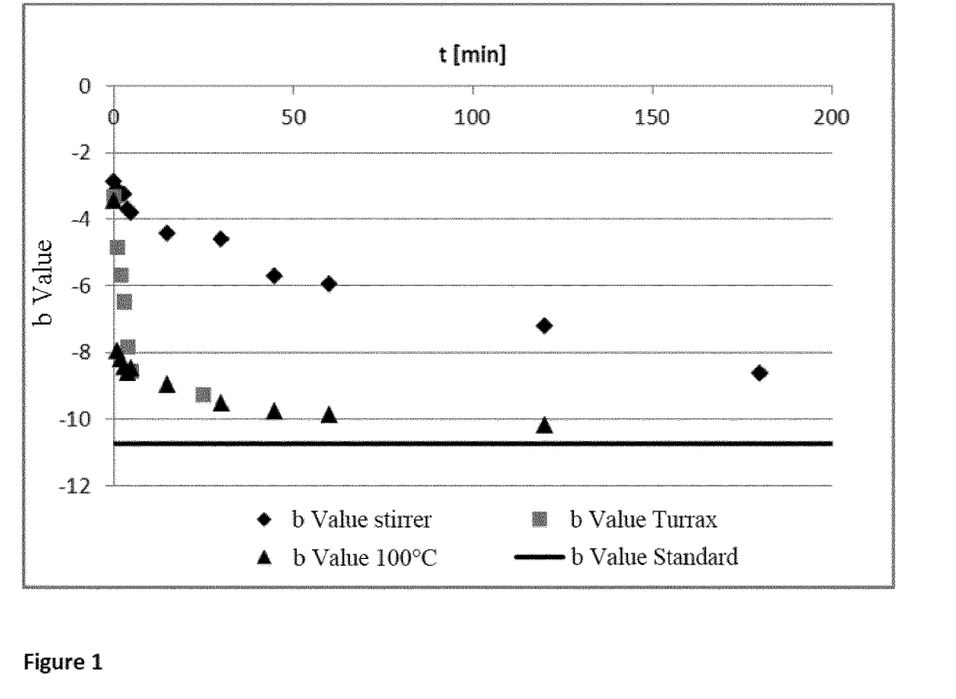
FIG. 1 is a graph of different release progressions over time.

In order to demonstrate what influence heating or high shearing by means of Ultra-Turrax have on the release behaviour, the capsules were dispersed with the coloured oil once again in neutral oil. One sample was only stirred and the blue colouration of the dispersion medium was measured. The second sample was highly sheared using Ultra-Turrax and the third sample was kept at a temperature of 100° C. The different release progressions are shown by reference to the "blue" value in FIG. 1.

Example 5

Aroma Release in a Chewing Gum Formulation

Figure 2:
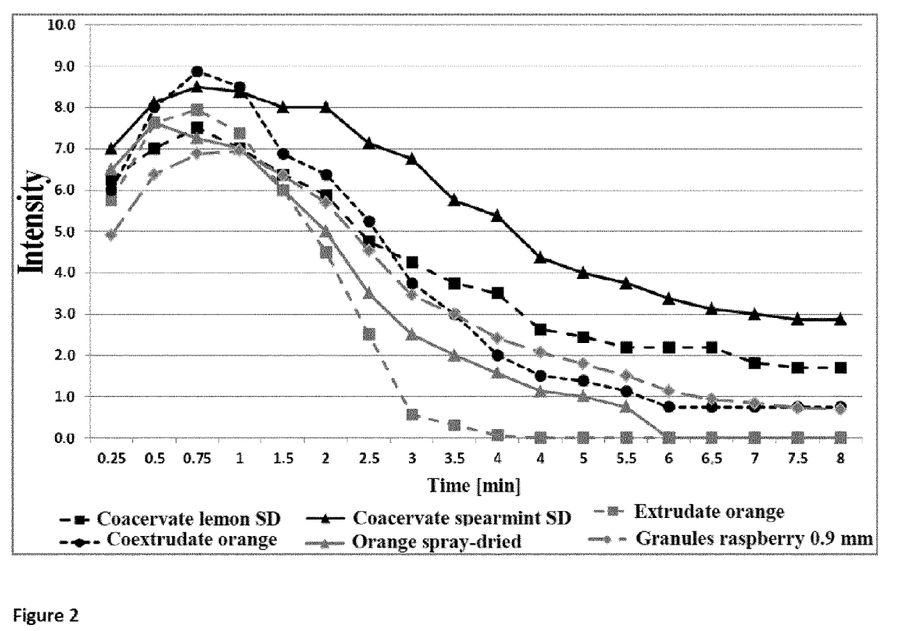
FIG. 2 is a graph of the release of aromas in chewing gum formulations over time.

A standard chewing gum formulation was admixed with identical amounts of different capsules containing lemon, orange and spearmint aroma and the release of the aromas was monitored over time (FIG. 2). It can be clearly seen that the new spray-dried coacervates release the aroma significantly more slowly and therefore bring about the long-lasting aroma release desired for chewing gum and thus also aroma perception.

Application Examples

Application Example 1

Table 2 below gives two formulations for an ice tea drink (black tea). Black tea extract was dissolved in water and stirred together with sugar; an aroma preparation and the Aronia extract A in a beaker.

TABLE 2

Application formulations

| Ingredient | Use in % by weight A | B |
|---|---|---|
| Black tea extract | 1.4 | 1.4 |
| Sugar | 7 | 7 |
| Citric acid (crystalline) | 1.2 | 1.2 |
| Ascorbic acid | 0.2 | 0.2 |
| Microcapsules according to Example 2 with cherry aroma | 1.0 | 1.5 |
| Water | ad 100 | |

Application Example 2

Table 3 below gives two further formulations for an ice tea drink (green tea, reduced sugar). Green tea extract was dissolved in water and stirred together with sugar and the sweetener saccharin and rebaudioside A, an aroma preparation, and the Aronia extract A in a beaker.

TABLE 3

Application formulations

| Ingredient | Use in % by weight A | B |
|---|---|---|
| Green tea extract | 1.4 | 1.4 |
| Sugar | 3.45 | 3.45 |
| Sweetener saccharin | 0.1 | — |
| Sweetener Rebaudioside A | — | 0.02 |
| Citric acid (crystalline) | 1.2 | 1.2 |
| Ascorbic acid | 0.2 | 0.2 |
| Microcapsules according to Example 2 with citrus aroma | 1.0 | 1.5 |
| Water | ad 100 | |

Application Example 3

Table 4 below gives two further formulations for an ice tea drink (black tea, sugar-free). Black tea extract was dissolved in water and stirred together with the sweetener saccharin, an aroma preparation, and also the Aronia extract A in a beaker.

TABLE 4

Application formulations

| Ingredient | Use in % by weight A | B |
|---|---|---|
| Black tea extract | 1.4 | 1.4 |
| Saccharin | 0.035 | 0.035 |
| Citric acid (crystalline) | 1.2 | 1.2 |
| Ascorbic acid | 0.2 | 0.2 |
| Microcapsules according to Example 2 with citrus aroma | 1.0 | 1.5 |
| Water | ad 100 | |

Application Example 4

Table 5 below gives formulations for a soya drink. The Aronia extract was added to soy milk from a local supermarket. The mixture was stirred together with the milk aroma in a beaker.

TABLE 5

Application formulations

| Ingredient | Use in % by weight A | B | C | D |
|---|---|---|---|---|
| Soya milk (non-aromatized, unsweetened) | ad 100 | | | |
| Saccharose | 3.0 | — | 1.5 | 2.0 |
| Sucralose | — | 0.025 | 0.01 | — |
| Na-saccharin | — | — | 0.01 | — |
| Emulgum | 0.1 | 0.1 | — | 0.1 |
| Microcapsules according to Example 2 with vanilla aroma | 0.5 | 0.75 | 1.0 | 1.5 |
| Hesperetin, 5% strength in ethanol | — | — | — | 0.1 |

Application Example 5

Table 6 below gives a formulation for a soya drink in combination with γ-aminobutyric acid. The γ-aminobutyric acid was predissolved in water and added together with the Aronia extract A to soy milk from a local supermarket. The resulting mixture was stirred together with the milk aroma in a beaker.

TABLE 6

Application formulations

| Ingredient | Use in % by weight |
|---|---|
| Soya milk (from local supermarket) | 98.3 |
| Microcapsules according to Example 2 with milk aroma | 1.5 |
| γ-Aminobutyric acid, 1% strength in water | 0.1 |

Application Example 6

Table 7 below gives a formulation for a grapefruit juice. The compounds (1) and (2) were pre-dissolved in ethanol and added to a grapefruit juice from a local supermarket. The resulting mixture was homogenized in a beaker by stirring.

TABLE 7

Application formulations

| Ingredient | Use in % by weight |
|---|---|
| Grapefruit juice (from local supermarket) | 98.5 |
| Microcapsules according to Example 2 with citrus aroma | 1.5 |

Application Example 7

Table 8 below gives two formulations for bitter chocolate. For this, a bitter chocolate was produced from the following raw materials and then poured into rectangular moulds:

TABLE 8

Application formulations

| Ingredient | Use in % by weight A | B |
|---|---|---|
| Coco mass | ad 100 | ad 100 |
| Cocoa butter | 11.70 | 11.70 |

TABLE 8-continued

Application formulations

| Ingredient | Use in % by weight A | Use in % by weight B |
|---|---|---|
| Sugar | 29.50 | 29.50 |
| Skimmed milk | 3.00 | 3.00 |
| Lecithin | 0.2 | 0.2 |
| Vanillin | 0.035 | 0.035 |
| Microcapsules according to Example 2 with chilli aroma | 1.0 | 1.5 |

Application Example 8

Table 9 below gives a formulation for a chewing gum. Parts A to D were mixed and intensively kneaded. The crude mass can be processed e.g. in the form of thin strips to give ready-to-consume chewing gums.

TABLE 9

Application formulations

| Part | Ingredient | Use in % by weight |
|---|---|---|
| A | Chewing gum base, Company "Jagum T" | 30.00 |
| B | Sorbitol, pulverized | 39.00 |
|   | Isomalt ® (Palatinit GmbH) | 9.50 |
|   | Xylitol | 2.00 |
|   | Mannitol | 3.00 |
|   | Aspartam ® | 0.10 |
|   | Acesulfam ® K | 0.10 |
|   | Emulgum ® (Colloides Naturals, Inc.) | 0.30 |
| C | Sorbitol, 70% strength in water | 14.00 |
|   | Glycerol | 1.00 |
| D | Microcapsules according to Example 2 with spearmint aroma | 1.00 |

Application Example 9

Table 10 below gives a formulation for a toothpaste. The ingredients of parts A and B were in each case premixed and stirred together thoroughly in vacuum at 25-30° C. for 30 min. Part C was premixed and added to A and B; D was added and the mixture was stirred thoroughly in vacuum at 25-30° C. for 30 min. Following decompression, the toothpaste was ready and was able to be transferred to a container.

TABLE 10

Application formulations

| Part | Ingredient | Use in % by weight |
|---|---|---|
| A | Demineralized water | 21.50 |
|   | Sorbitol (70%) | 45.00 |
|   | Solbrol ® M, sodium salt (Bayer AG, p-hydroxybenzoic acid alkylester) | 0.15 |
|   | Trisodium phosphate | 0.10 |
|   | Saccharin, 450x | 0.20 |
|   | Sodium monofluorophosphate | 1.12 |
|   | Polyethylene glycol 1500 | 5.00 |
| B | Sident 9 (abrasive silicon dioxide) | 10.00 |
|   | Sident 22 S (thickening silicon dioxide) | 8.00 |
|   | Sodium carboxymethylcellulose | 0.90 |
|   | Titanium dioxide | 0.50 |
| C | Demineralized water | 4.53 |
|   | Sodium lauryl sulphate | 1.50 |

TABLE 10-continued

Application formulations

| Part | Ingredient | Use in % by weight |
|---|---|---|
| D | Microcapsules according to Example 2 with mint aroma | 1.50 |

What is claimed is:

1. A process for producing controlled release active ingredient capsules, consisting essentially of:
    (a) dissolving and/or dispersing (a1) proteins, (a2) polysaccharides and (a3) cellulose derivatives in water with the input of mechanical and thermal energy to form a coacervate,
    (b) adding active ingredients to be encapsulated to the coacervate to form active ingredient capsules,
    (c) hardening the resulting active ingredient capsules with the addition of natural tannins, in the absence of glutaric aldehyde and formaldehyde for a period of 5 to 10 hours, and
    (d) optionally, spray-drying the hardened active ingredient capsules and wherein the process occurs in a maximum of 12 hours;
    wherein the process is conducted with half of the water that would be required if cellulose derivatives (a3) were not used in the process.

2. The process according to claim 1, wherein the proteins (a1) used are gelatines which have a gel strength of from 100 to 300 Bloom.

3. The process according to claim 1, wherein the polysaccharides (a2) are selected from the group consisting of pectins, xanthans, gum arabic, agaroses, and mixtures thereof.

4. The process according to claim 1, wherein the cellulose derivatives (a3) are cellulose ethers or cellulose esters which have a degree of substitution above 80%.

5. The process according to claim 1, wherein the active ingredients are aromas or perfume oils.

6. The process according to claim 1, wherein the components a1, a2 and a3 are used in the weight ratio of a1:a2:a3, wherein a1 is about 10, a2 is about 1 to 5, and a3 is about 0.5 to 2.

7. The process according to claim 1, wherein the components a1+a2+a3 to the active ingredients to be encapsulated are used in the weight ratio of about 5 to 15:1.

8. The process according to claim 1, wherein step (a) is carried out at temperatures in the range from about 20 to about 90° C.

9. The process according to claim 1, wherein, the, natural tannins are added in an amount of from about 0.1 to about 2% by weight based on the weight of the active ingredient capsules formed in step (b).

10. The process according to claim 1, wherein the hardened capsules are spray-dried in the presence of polysaccharides.

11. The process of claim 1 wherein active ingredient capsule produced therefrom has a breaking strength equivalent to a process that employs a formaldehyde or glutaraldehyde crosslinker.

12. The process of claim 1 wherein the active ingredient capsules produced therefrom have a D50 value of from 50 µm to about 100 µm.

* * * * *